(12) United States Patent
Yang et al.

(10) Patent No.: US 12,070,289 B2
(45) Date of Patent: Aug. 27, 2024

(54) JOINT COMPONENT

(71) Applicant: IP2IPO INNOVATIONS LIMITED, London (GB)

(72) Inventors: Guang-Zhong Yang, London (GB); Pierre Berthet-Rayne, London (GB); Kiyoung Kim, London (GB)

(73) Assignee: IP2IPO Innovations Limited, London (GB)

( * ) Notice: Subject to any disclaimer, the term of this patent is extended or adjusted under 35 U.S.C. 154(b) by 1036 days.

(21) Appl. No.: 16/964,404

(22) PCT Filed: Jan. 24, 2019

(86) PCT No.: PCT/GB2019/050208
§ 371 (c)(1),
(2) Date: Jul. 23, 2020

(87) PCT Pub. No.: WO2019/145725
PCT Pub. Date: Aug. 1, 2019

(65) Prior Publication Data
US 2021/0045821 A1 Feb. 18, 2021

(30) Foreign Application Priority Data
Jan. 26, 2018 (GB) ...................................... 1801338

(51) Int. Cl.
*A61B 34/30* (2016.01)
*A61B 34/00* (2016.01)
(Continued)

(52) U.S. Cl.
CPC .............. *A61B 34/71* (2016.02); *A61B 34/30* (2016.02); *B25J 9/1075* (2013.01); *F16C 11/04* (2013.01);
(Continued)

(58) Field of Classification Search
CPC ... A61B 34/71; A61B 34/30; A61B 2034/301; A61B 2034/306; A61B 1/008; A61B 1/0055; B25J 9/1075; F16C 11/04
See application file for complete search history.

(56) References Cited

U.S. PATENT DOCUMENTS

2011/0152879 A1* 6/2011 Williams ............... A61B 34/71
606/130
2014/0257331 A1 9/2014 Kim et al.
(Continued)

FOREIGN PATENT DOCUMENTS

CN 206714730 U 12/2017
EP 1679046 A2 12/2006
(Continued)

OTHER PUBLICATIONS

International Search Report & Written Opinion dated May 6, 2019; PCT Application No. PCT/GB2019/050208; pp. 1-12.
(Continued)

*Primary Examiner* — Eugene T Wu

(74) *Attorney, Agent, or Firm* — FisherBroyles LLP; Kevin D. Jablonski

(57) ABSTRACT

A surgical instrument having a proximal end, a distal end and a shaft, the shaft comprising a plurality of joint components connected in series, each joint component comprising first and second connectors, which connectors are axially spaced apart from one another at first and second ends of a respective joint component, characterised in that the first connector comprises a first rolling surface, and the second
(Continued)

connector comprise a second rolling surface, and wherein each joint component comprises a first spur gear extending from the first rolling surface, and a second spur gear extending from the second rolling surface, wherein the first rolling surface of a first joint component is engageable with the second rolling surface of a second joint component to form a rolling joint, and the second rolling surface of the first joint component is engageable with a first rolling surface of a third rolling joint.

21 Claims, 11 Drawing Sheets

(51) Int. Cl.
    *B25J 9/10*     (2006.01)
    *F16C 11/04*     (2006.01)
(52) U.S. Cl.
    CPC ... *A61B 2034/301* (2016.02); *A61B 2034/306* (2016.02)

(56) References Cited

U.S. PATENT DOCUMENTS

| | | |
|---|---|---|
| 2015/0202013 A1 | 7/2015 | Teichtmann et al. |
| 2016/0022365 A1* | 1/2016 | Jensen ............... F16H 55/0813 74/96 |
| 2017/0231686 A1* | 8/2017 | Sartor ................ A61B 18/149 606/46 |

FOREIGN PATENT DOCUMENTS

| | | |
|---|---|---|
| EP | 3263291 A1 | 3/2018 |
| KR | 20130027688 A | 3/2013 |
| WO | 2008126470 A1 | 10/2008 |
| WO | 2018058007 A1 | 3/2018 |

OTHER PUBLICATIONS

Combined Search & Examination Report under Section 17 and 18(3) dated Jul. 24, 2018; Great Britain Patent Application No. 1801338.3; pp. 1-8.

* cited by examiner

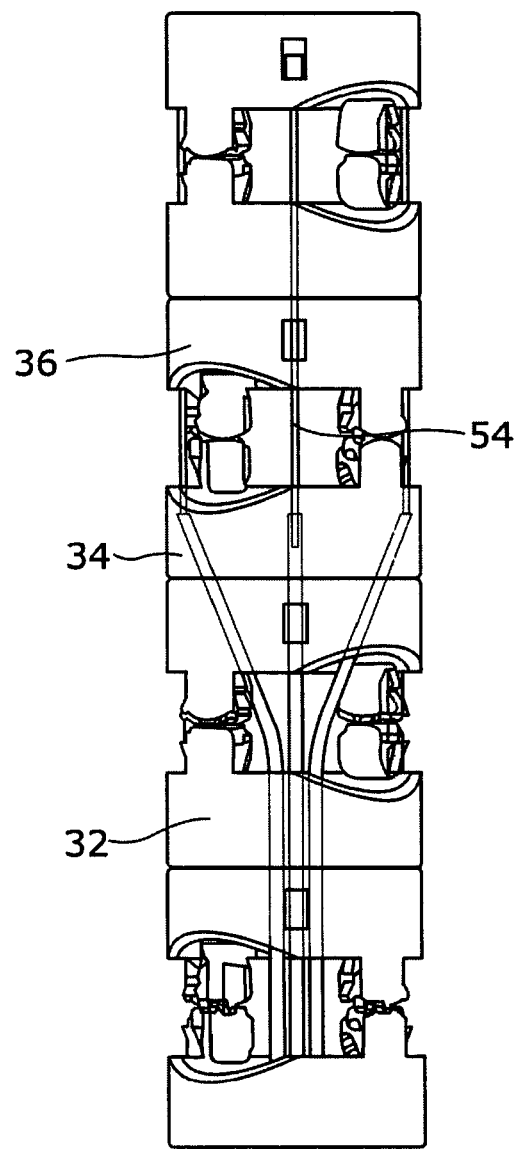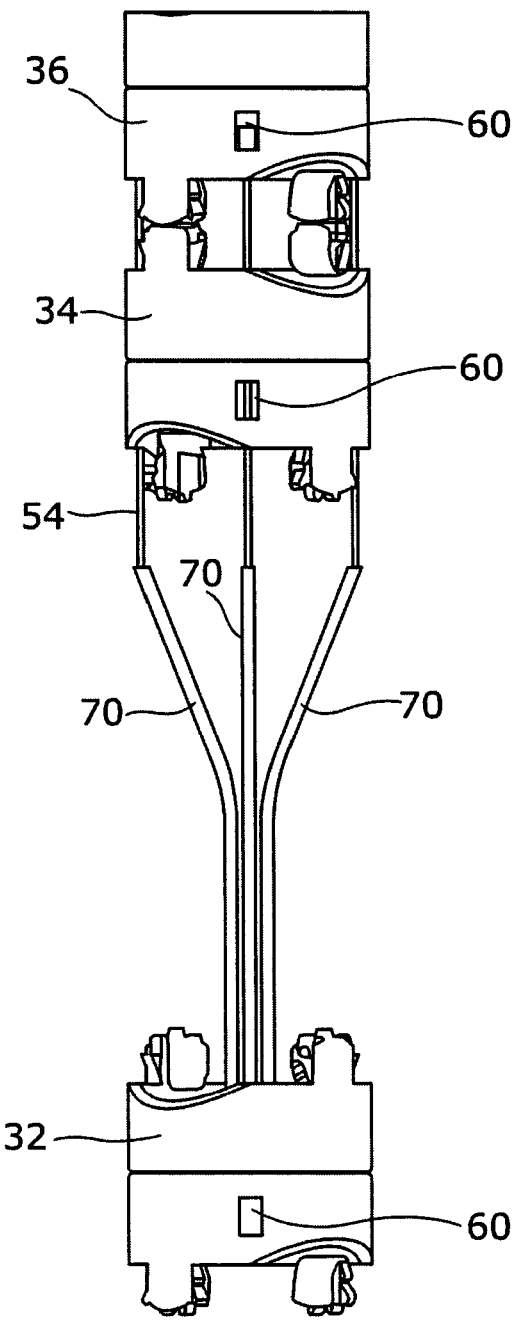
Figure 4
Figure 5

JOINT COMPONENT

TECHNOLOGICAL FIELD

Embodiments of the invention relate to a joint component for a surgical instrument, and particularly, but not exclusively, to a joint component for a surgical instrument for use in natural orifice surgery. Embodiments of the invention also relate to a surgical instrument formed from a plurality of the joint components and to a method of operating the surgical instrument. Such a surgical instrument may be in the form of a snake-like robot.

BACKGROUND

The use of snake-like robots for surgery has become a popular choice for intraluminal procedures.

In known devices, it can be difficult to meet the requirements for strength, flexibility and accuracy simultaneously in a single instrument.

Known snake-like robots are bio-inspired mechatronic devices with a flexible actuated body, allowing the entire system to navigate inside the human anatomy and perform specific surgical tasks. Snake-like robots present many advantages compared to conventional surgical robots. First, their size is smaller, allowing a surgeon to use the robots to reach confined regions and deep-seated lesions. Secondly their body is flexible and can follow natural pathways, offering a broad range of potential surgical procedures through natural orifices. Finally, they require less incisions or even no incisions leading ultimately to less patient trauma. It is envisaged that the evolution of such devices will have a positive impact on minimal invasive surgery.

In order to perform these tasks, a surgical snake robot should have the following features:
- a narrow body to navigate through small incisions and natural orifices;
- redundant degrees of freedom to allow full retroflection and to navigate through natural human pathways;
- high quality vision or stereo-vision and adequate lighting.

In addition, the robot should have multiple tool channels and have a complete range of tools which can be easily exchanged during a procedure to ensure appropriate tools are available at all times.

It is also desirable for such snake robots to be patient specific to ensure a custom fit to uncommon anatomies.

Known rolling joints have three major disadvantages:
1. the surfaces may move asynchronously due to slippage, resulting in uncontrolled motion;
2. the surfaces can slip if the joint moves sideways, resulting in a dislocated joint; and
3. the modelling of the rolling joint is more complex than a standard pivot point, resulting in more complex control algorithms being necessary.

SUMMARY

According to a first aspect of embodiments of the present invention there is provided a surgical instrument having a proximal end, a distal end and a shaft, the shaft comprising a plurality of joint components connected in series, each joint component comprising first and second connectors, which connectors are axially spaced apart from one another at first and second ends of a respective joint component, characterised in that the first connector comprises a first rolling surface, and the second connector comprise a second rolling surface, and wherein each joint component comprises a first spur gear extending from the first rolling surface, and a second spur gear extending from the second rolling surface, wherein the first rolling surface of a first joint component is engageable with the second rolling surface of a second joint component to form a rolling joint, and the second rolling surface of the first joint component is engageable with a first rolling surface of a third joint component.

By means of embodiments of the present invention, a surgical instrument is provided by a plurality of joint components connected in series along the shaft of the surgical instrument. The joint components are engageable with one another to form rolling joints, which rolling joints are spaced apart axially along the shaft of the surgical instrument.

The surgical instrument according to embodiments of the invention may comprise, as well as the plurality of joint components, other components. In other words, the shaft may comprise components other than the joint components.

A rolling joint is a mechanical structure where two curved surfaces roll against each other. A rolling joint offers advantages such as limited friction, since the surfaces roll against each other, leading to large force transmission capabilities.

When adjacent joint components come together to form a joint, the two spur gears will engage with one another in a normal manner, thus limiting movement between adjacent joint components.

The use of a spur gear sandwiched between two rolling surfaces ensures that both surfaces roll in a controlled motion, and that they do not side slip. This results a smooth controlled motion across the full range of the joint.

The presence of the spur gears means that whilst adjacent joint components continue to roll against each other, the possibility of sideways movement is reduced or eliminated thus removing or reducing the possibility that joints will dislocate.

In addition, the presence of the spur gears prevents or reduces the possibility of asynchronous movement due to slippage. Such movement may result in uncontrolled motion.

The resulting rolling joint formed between two joint components in accordance with embodiments of the first aspect is thus a synchronous bi-stable rolling joint.

The rolling joint forming part of the surgical instrument according to embodiments of the present invention is a bio-inspired serial link that may be regarded as two circular surfaces rolling against each other. In nature such joints may be found in the bone joints of many living species including the human knee, phalanges, etc. Whilst the presence of a spur gear extending from a rolling surface limits movement between two adjacent joints, it nevertheless allows rolling movement between adjacent joint components albeit in a restricted manner.

A rolling joint offers advantages such as limited friction, since the surfaces of the joints roll against each other leading to large force transmission capabilities. Another advantage of a rolling joint is that it can be designed in a way in which the actuation is symmetric, therefore reducing backlash when tendons are used for activation. Finally, because the surfaces roll against each other, the number of parts required to be assembled is reduced.

In embodiments of the invention, each joint component comprises two first connectors and two second connectors, the first connectors being positioned at the first end of the joint component, and the second connectors being positioned at the second end of the joint component, and wherein each joint component comprises two first spur gears and two second spur gears, each spur gear extending from a respective rolling surface.

In such embodiments of the invention a rolling joint is formed between two first connectors of a first joint component and two second connectors of a second joint component.

In such embodiments of the invention the two first connectors are positioned opposite to one another at the first end of a respective joint component, and the two second connectors are positioned opposite one another at the second end of the respective joint component, the second connectors being approximately 90° out of phase with the first connectors.

Such an arrangement means that when first and second joint components are brought into engagement with one another the direction of movement between the first and second joint components will be determined by the positioning of the first connectors of the first joint component and the second connectors of the second joint component. In addition, when a third joint component is brought into engagement with the first joint component such that a second rolling surface of the first joint component engages with a first rolling surface of the third joint components, movement between the third joint component and the first joint component may be different to the movement between the first and second joint components.

Depending on how the joint components are driven, a range of different movements between adjacent joint components may be achieved.

In embodiments of the invention, each joint component has a substantially circular cross-section, with the two first connectors being diametrically opposed to one another along a first diameter, and the two second connectors being diametrically opposed to one another along a second diameter, the first and second diameters being substantially orthogonal to one another.

In some embodiments of the invention the joint component comprises a wall defining a hollow interior.

The hollow interior may be useful to allow cables and instruments through the surgical instrument. By creating a hollow interior, cables and instruments may be readily passed through the surgical instrument.

In embodiments of the invention, each joint component comprises an inner channel extending axially through the joint component.

The inner channel may be substantially co-axial with the joint component and thus the surgical instrument and may be adapted to carry cables and/or instruments. This inner channel is particularly suitable for carrying cables and tendons which may be used to drive the joint components as will be described in more detail below.

In some embodiments of the invention the inner channel of each joint component comprises a central channel and a peripheral channel extending from the central channel portion to an inner surface of the outer wall.

In some embodiments of the invention there may be a plurality of peripheral channels extending from the central channel portion in the inner surface of the outer wall. In some embodiments of the invention there are four peripheral channels each extending substantially at right angles from the inner channel in a cross-shaped configuration. However, in other embodiments of the invention there may be a different number of peripheral channels arranged in a different formation.

The one or more peripheral channels may extend in a direction substantially at right angles to the axis of the joint component. However, in other embodiments of the invention, the peripheral channel or channels extend in a direction forming an angle of greater than 0° and less than 90°, or greater than 90° and less than 180° with the axis of the joint component. In such embodiments of the invention the peripheral channel or channels may be described as an angled channel or channels.

In embodiments of the invention, each joint component may further comprise a wall channel extending axially along an inner surface of the wall. In such embodiments of the invention, the peripheral channel or channels may extend from the central channel to the wall channel.

The surgical instrument may comprise a plurality of joint units, each joint unit comprising three joint components.

In such embodiments of the invention, a surgical instrument may be assembled by connecting in series a plurality of joint units. Each joint unit will comprise two rolling joints and three joint components.

The surgical instrument may comprise other components in addition to the plurality of joint units and may for example comprise one or more joint components not forming part of a joint unit.

In some embodiments of the invention, the surgical instrument comprises a drive mechanism for driving the joint components.

In embodiments of the invention the drive mechanism comprises a plurality of tendons.

The tendons will extend from the proximal end of the surgical instrument to a predetermined joint component. This means that all tendons required to drive the joint components forming the surgical instrument will extend through the surgical instrument and will be diverted to a predetermined joint component.

In embodiments of the invention in which each joint component comprises an inner channel, the tendons may extend through the inner channel and then may be diverted to appropriate joint components via the peripheral channels. In such embodiments of the invention, the peripheral channels may comprise angled channels.

In such embodiments of the invention, there may be a single peripheral channel for each tendon being diverted to the predetermined joint component.

In embodiments of the invention, tendons may be operated in pairs in order to cause movement of particular rolling joints.

In some embodiments of the invention in which the surgical instrument comprises a plurality of joint units, each joint unit may comprise first, second and third joint components. In such embodiments of the invention, two pairs of tendons may be attached to each of the first and third joint components. In such embodiments of the invention the second, or middle joint component positioned between the first and third joint components may be regarded as a floating joint component.

In embodiments of the invention at least one joint component comprises a tendon attachment portion for attaching tendons to the joint component.

In embodiments of the invention at least one joint component comprises a plurality of tendon attachment portions each of which portions is adapted to fix one tendon to the joint component.

In embodiments of the invention were two pairs of tendons are attached to a joint component, each joint component may comprise four tendon attachment portions each of which is adapted to attach a single tendon to the joint component.

Since in at least some embodiments of the invention, tendons will not be attached to all joint components, some of the joint components may not include tendon attachment portions. However, in other embodiments of the invention, all of the joint components will be substantially identical to one another to allow the surgical instrument to be readily redesigned. In other words, if all the joint components are substantially identical to one another, then each joint component may be used in any desired way in order to form a surgical instrument having appropriate dimensions and other properties.

In embodiments of the invention the surgical instrument further comprises an actuator for controlling movement of the drive mechanism.

The actuator may comprise a motor operatively connected to the tendons. In some embodiments of the invention the actuator may comprise a plurality of motors. In some embodiments of the invention where pairs of tendons are used to cause movement of rolling joints, the actuator may comprise a separate motor for driving each pair of tendons. In other embodiments of the invention, a plurality of tendons may be coupled together so that a plurality of tendons may be driven by a single motor.

In general, each degree of freedom of the surgical instrument will require a motor to drive the tendons responsible for movement in relation to a particular degree of freedom. In an embodiment of the invention having 13 degrees of freedom, the degrees of freedom may be coupled to effectively reduce the degrees of freedom from thirteen to seven. In such an embodiment seven motors will be required to drive the tendons forming the surgical instrument.

The actuator may be positioned outside the body of the surgical instrument.

Such an arrangement allows the surgical instrument itself to have small dimensions when required since the surgical instrument is not required to house the actuator.

In embodiments of the invention, the actuator further comprises a switch for controlling connection of a motor to an associated pair of tendons.

The switch may comprise a three-way switch, and in some embodiments of the invention the switch may comprise a mechanical three-way switch.

In some embodiments of the invention the switch comprises a differential mechanism coupled with an electromagnetic brake.

In embodiments of the invention incorporating a three-way switch, the surgical instrument may have an actuation state, a stiff state, and a floppy state.

In the floppy state, all the joint components are disengaged from the motors and the surgical instrument is manually back driveable.

The actuation state may be used for follow-the-leader navigation and for inspection of a patient's anatomy for example. In the actuation state, the joint components are engaged with the motor.

In the stiff state, the joint components cannot move relative to one another and the surgical device will be rigid.

In such embodiments of the invention, the surgical instrument may be switched into the floppy state when it is required to manually insert or retract the surgical instrument for example during a standard endoscopic procedure.

The surgical instrument may be switched into the actuation state in order to allow follow-the-leader navigation and inspection of a patient's anatomy, for example.

Finally, the surgical instrument may be switched to the stiff state when, for example a stable platform is required to perform issue manipulation.

According to a second aspect of the invention there is provided a joint component forming part of the surgical instrument according to the first aspect of the invention.

According to a third aspect of the invention there is provided a joint unit forming part of the surgical instrument according to the first aspect of the invention.

According to a fourth aspect of the invention there is provided a method of operating a surgical instrument, the instrument comprising: a proximal end, a distal end and a shaft, the shaft comprising a plurality of joint components connected in series, each joint component comprising first and second connectors, which connectors are axially spaced apart from one another at first and second ends of a respective joint component, characterised in that the first connector comprises a first rolling surface, and the second connector comprise a second rolling surface, and wherein each joint component comprises a first spur gear extending from the first rolling surface, and a second spur gear extending from the second rolling surface, wherein the first rolling surface of a first joint component is engageable with the second rolling surface of a second joint component to form a rolling joint, and the second rolling surface of the first joint component is engageable with a first rolling surface of a third rolling joint, the surgical instrument further comprising a drive mechanism for driving the joint components which drive mechanism comprises a three way switch for controlling connection of a motor to the drive mechanism in order to switch the surgical instrument between a floppy state in which the joint components are disengaged from the drive mechanism, an actuation state in which the joint components are engaged with the drive mechanism and a stiff state in which the surgical instrument joint components cannot move. The method comprising the steps of:

inserting the surgical instrument into a patient via a natural orifice or incision;
  switching the instrument to an actuation state;
  carrying out a required medical procedure; and then
  removing the instrument from the patient.

The method may comprise an initial step carried out before the step of inserting the surgical instrument, of switching the surgical instrument into the floppy state.

In other embodiments of the invention, the initial step comprises the step of switching the surgical instrument into the stiff state.

The method may comprise a further step carried out after carrying out the required medical procedure, of switching the instrument to a floppy state or a stiff state to thereby remove the instrument from the patient.

BRIEF DESCRIPTION OF THE DRAWINGS

Embodiments of the invention will now be described by way of example only with reference to the accompanying drawings in which:

FIG. 4 is a schematic representation of a plurality of the joint units forming the surgical instrument of FIG. 1 showing tendons passing through the instrument;

FIG. 5 is a schematic representation of the joint units of FIG. 4 with some of the joint units removed to show the route taken by the tendons and Bowden cables;

FIGS. 8 to 11 are schematic representations of a switch in the form a differential mechanism for controlling the connection between a motor, and a brake and the tendons in the surgical instrument illustrated in FIG. 1a;

FIG. 12 is a schematic representation of a back drivable actuation pack forming part of the surgical instrument shown in FIG. 1a;

FIG. 13 is a schematic representation of an alternative back driveable actuation pack that could be used to drive the surgical instrument as shown in FIG. 1a.

DETAILED DESCRIPTION

Figure 1A:
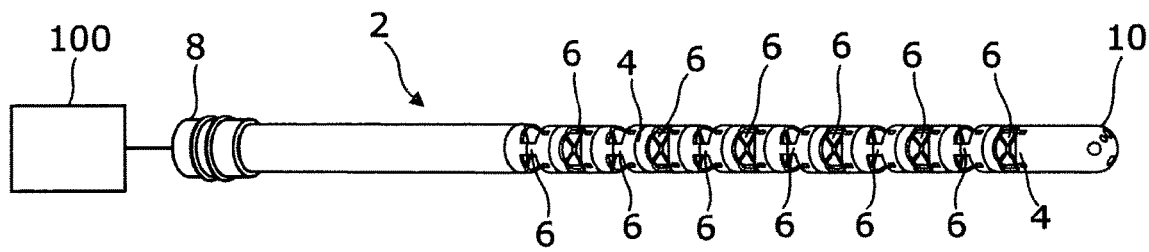
FIG. 1a is schematic representation of a surgical instrument made in accordance with embodiments of the first aspect of an embodiment of the invention.

Referring to the figures, a surgical instrument according to a first aspect of the embodiments of present invention is designated generally by the reference numeral 2. The surgical instrument 2 is in the form of a snake-like robot which may be used for many medical procedures such as intraluminal procedures and procedures which use the natural orifices of a patient in order to carry out the procedure.

The surgical instrument 2 comprises a plurality of joint components 4 which are linked together in series as will be described in more detail below. The joint components may be regarded as vertebrae.

The surgical instrument comprises a proximal end 8 and a distal end 10, and the joints 6 extend along an axis of the surgical instrument 2 between the proximal end and the distal end.

The surgical instrument 2 further comprises an actuator 100 which is operatively connected to the surgical instrument 2 at the proximal end thereof.

Each joint 4 comprises two first connectors 12 positioned at a first end 14 of the joint, and two second connectors 16 spaced apart from the first connectors 12 at a second end 18 of the joint 4. Each of the first connectors 12 comprises a first rolling surface 20, and each of the second connectors 14, 16 comprises a second rolling surface 22.

First spur gears 24 extend from each of the first rolling surfaces 20, and second spur gears 26 extend from the second rolling surfaces 22.

When adjacent joint components 4 engage with one another, the first spur gears 24 on one joint component 4 will engage with the second spur gears 26 on a second joint component 4. When adjacent joint components 4 engage with one another in this manner, a rolling joint 6 is formed. The spur gears 24, 26 reduce the likelihood that one joint component 4 will slip relative to the adjacent joint component 4 during movement of the joint formed by the two joint components.

The second connectors 16 of each joint component 4 are also spaced apart from one another at the second end 18 of the joint component 4. However, the second connectors 16 are offset from the first connectors 12 by, in this example, about 90°. This means that a different range of movement may be possible between for example a first and third joint component and a first and second joint components.

In this embodiment of the invention, the joint components 4 are arranged to form joint units 30 as shown in FIGS. 2a to 2c and 3a to 3c, for example. Each joint unit comprises first, second and third joint components 32, 34, 36 respectively. Due to the orientation of the first and second connectors 12, 16, and 18 on each joint component, a different range of movement may be possible at the rolling joint 6 formed between the second and third joint components 34, 36, than at the rolling joint 6 formed between the first 32 and second 34 joint components. The movement of the rolling joint 6 will be described in more detail below.

Figure 6:
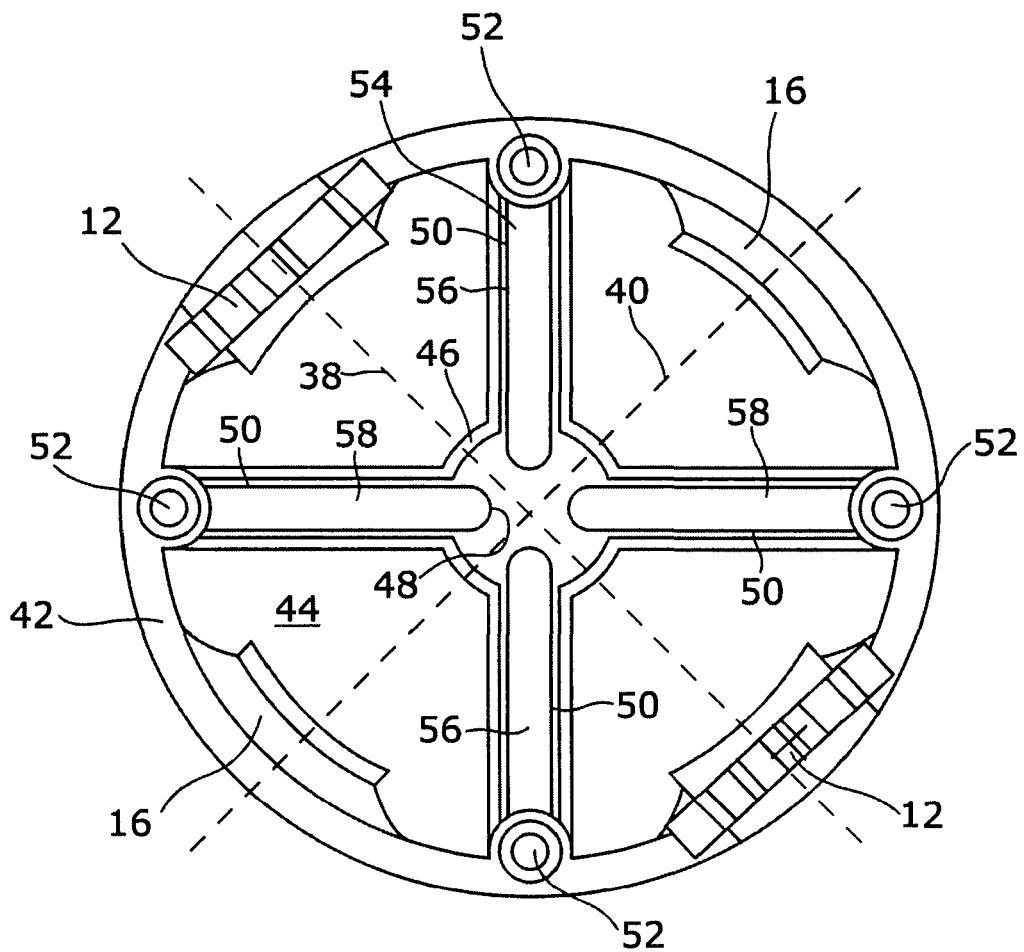
FIG. 6 is a top view representation of one of the joint components forming the surgical instrument of FIG. 1a showing the hollow interior of the joint component.

In this embodiment of the invention, each joint component 4 is substantially circular in cross-section as shown in FIG. 6. In this embodiment therefore the first connectors 12 are positioned diametrically opposed from one another along a first diameter 38 and the second connectors 16 are also positioned diametrically opposed to one another along a second diameter 40 to one another, but offset such that the first diameter 38 is substantially orthogonal to the second diameter 40.

The surgical instrument 2 has thirteen possible degrees of freedom, comprising 12 rolling joints 6, and a revolute joint 101 at the proximal end 8 of the instrument 2. It is to be understood, however, that in other embodiments of the invention the surgical instrument may have a different number of degrees of freedom.

Figure 1B:
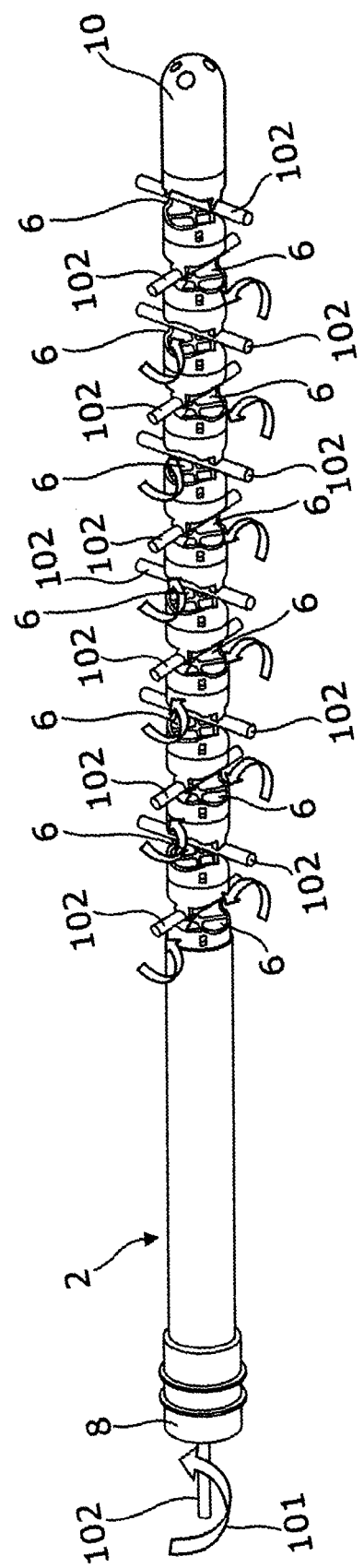
FIG. 1b is a schematic representation of the surgical instrument of FIG. 1a showing the degrees of freedom of the instrument.
Figures 3A, 3B, 3C:
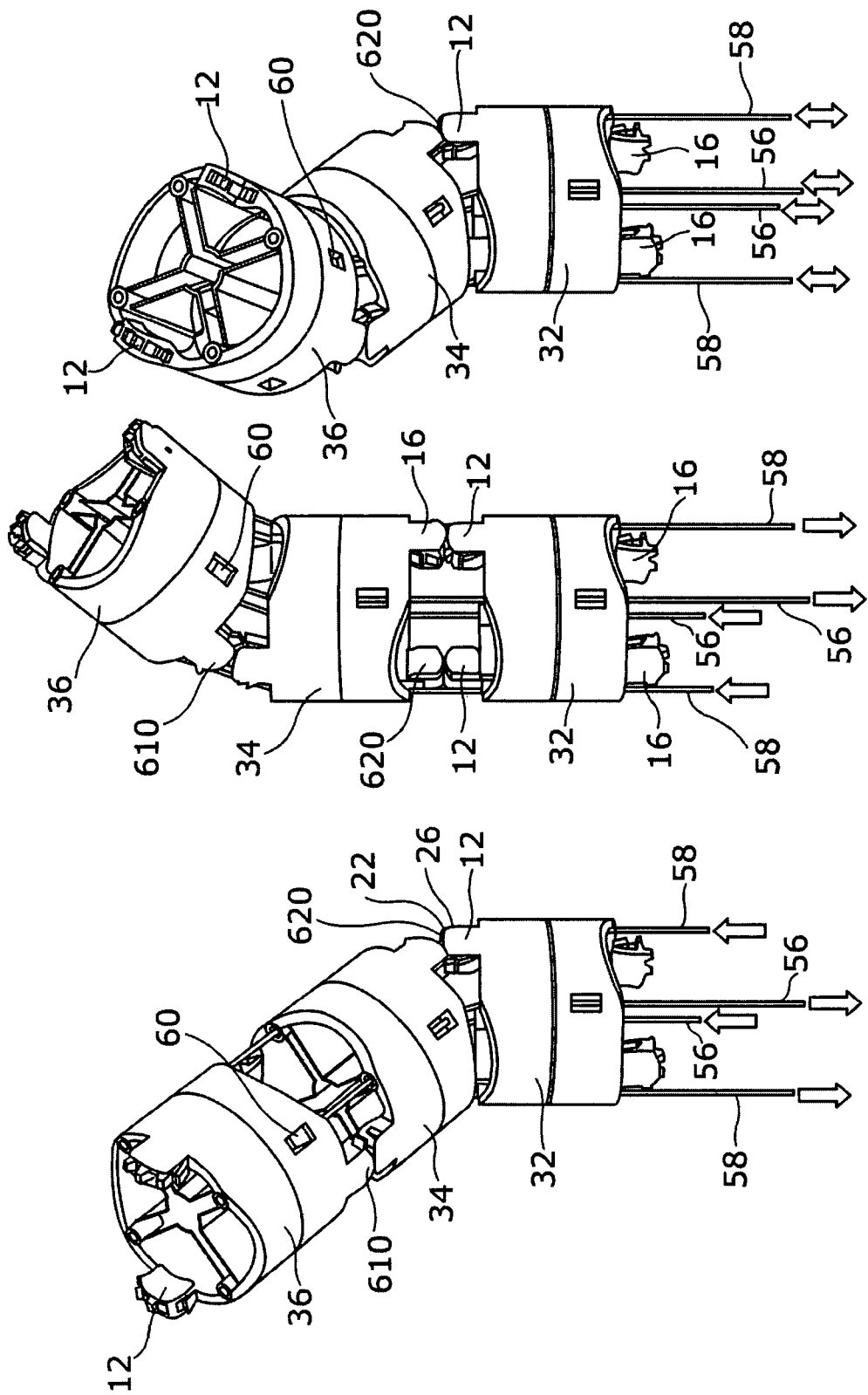
FIGS. 3a to 3c are schematic representations of the joint units shown in FIGS. 2a to 2c showing movement between the joint units.

These degrees of freedom are illustrated in FIG. 1b by rods 102. It is to be understood that the rods 102 do not exist in embodiments of the invention but are included in FIG. 1b to illustrate the degrees of freedom in the instrument.

Because of the way the that the joint components 4 are arranged to form joint units 30, parallel adjacent rods 102 are coupled together reducing the effective number of degrees of freedom to 7.

Figure 7A:
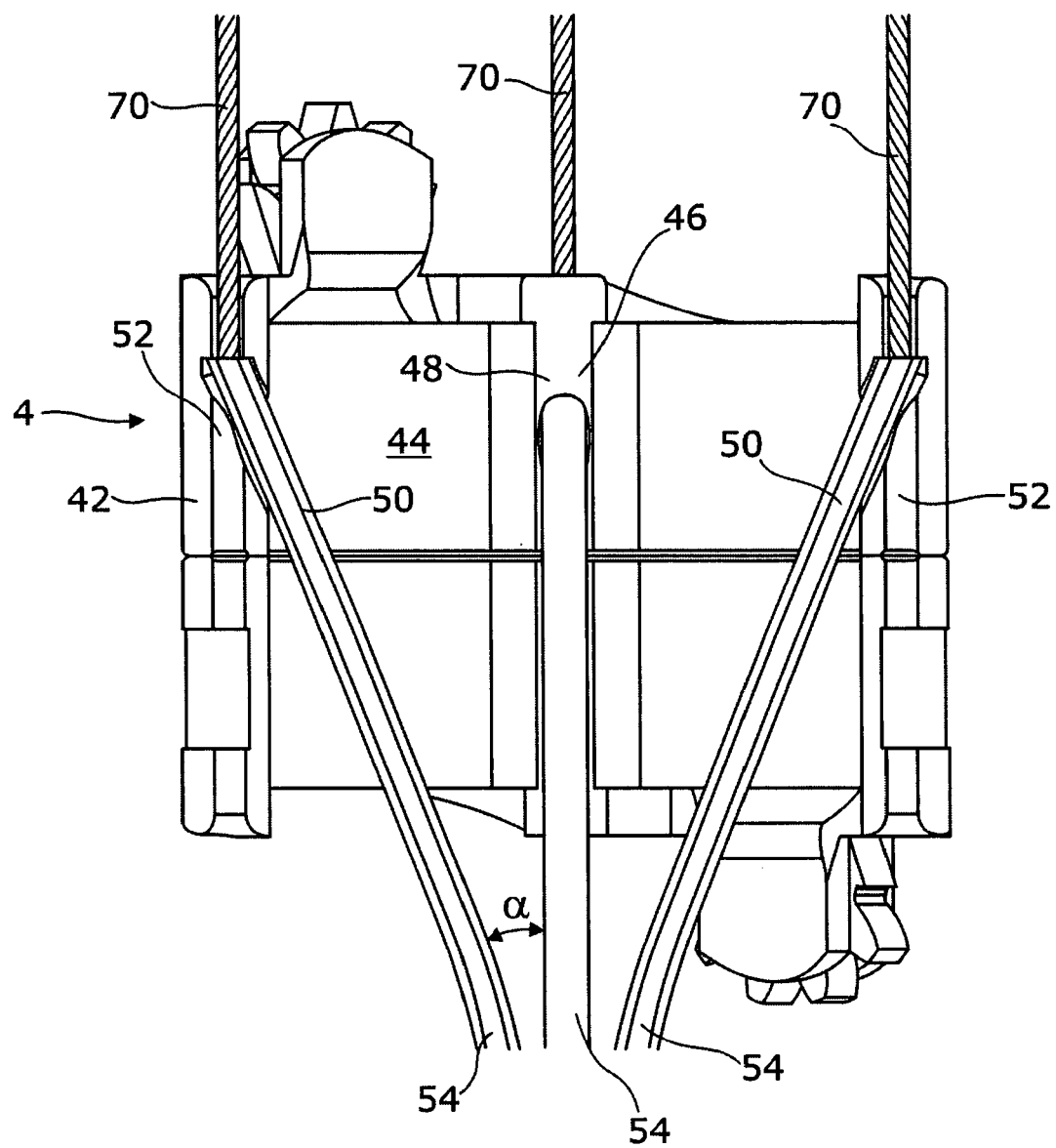
FIGS. 7a and 7b are a cross sectional representations of one of the joint components forming the surgical instrument of FIG. 4 showing the angled channels.
Figure 7B:
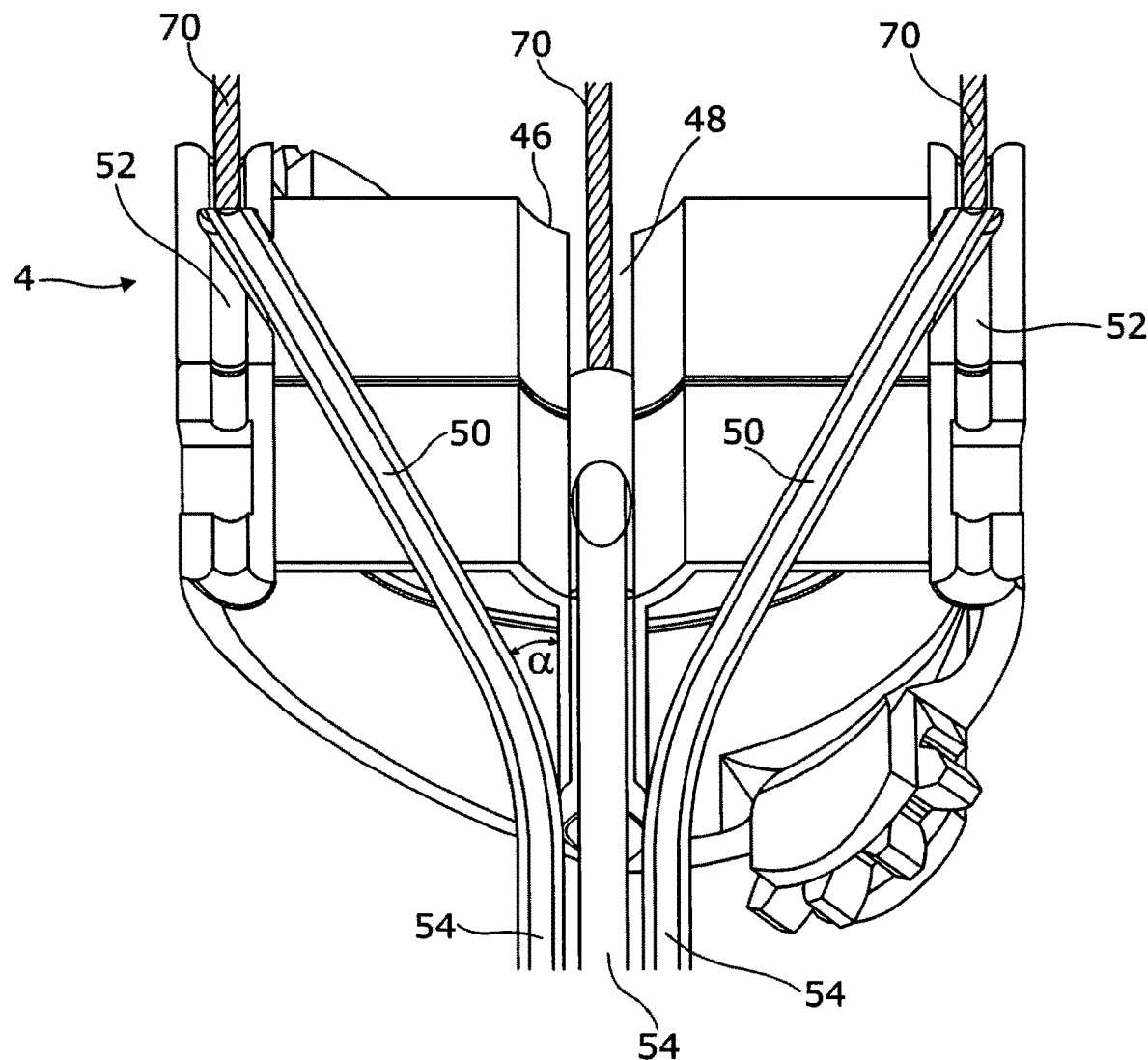
Figure 8:
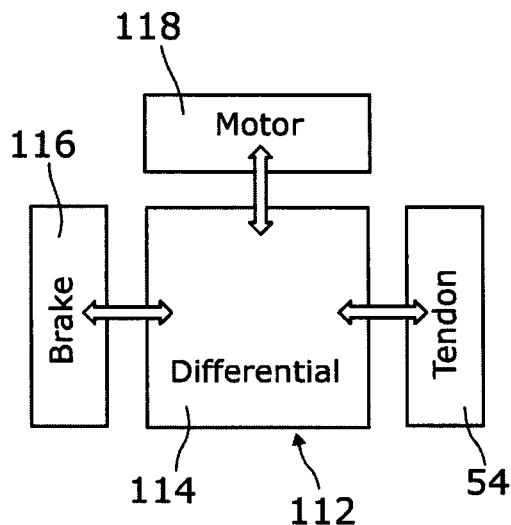

As also shown in FIGS. 6, 7a and 7b, each joint component 4 comprises a wall 42 which defines a hollow interior 44 of the joint component 4. In the illustrated embodiments, each joint component 4 further comprises an inner channel 46 extending axially through the joint component 4. The inner channel 46, in this embodiment comprises a central portion 48 and four peripheral channels 50 each of which peripheral channels 50 extends to the wall 42. Each joint component 4 further comprises wall channels 52 (in this case 4). In this embodiment of the invention there is a wall channel 52 positioned at the end of each peripheral channel 50.

In this embodiment of the invention the peripheral channels 50 extend in a direction that forms an angle α of less than 90° with the axis of the joint component 4. In other words, the peripheral channels 50 are angled relative to the inner channel 46 as shown in FIGS. 7a and 7b.

In the embodiment of the invention, the joints 6 are driven by tendons 54, arranged in pairs in order to control movement of the rolling joints 6. In this embodiment of the invention two pairs of tendons will be attached to a particular joint component 4 in order to control between them two rolling joints, as will be described in more detail below.

With respect to the joint unit 30 shown in FIGS. 2a, 2b and 2c, and 3a, 3b and 3c two pairs of tendons 56, 58 are used to control movement of rolling joints 610 and 620 respectively. The rolling joint 610 is formed between joint components 34 and 36 and rolling joint 320 is formed between rolling joints 32 and 34.

Both of the pairs of tendons 56, 58 are attached to the third joint component 36 at tendon attachment portions 60. The tendon pairs 56, 58 will extend from the tendon attachment portions 60 within Bowden cables 70 which extend through the surgical instrument down to the proximal end 8 of the surgical instrument where the tendons 56, 58 will be operatively connected to actuator 100. The two pairs 56, 58 of tendons are used to control movement of both of the rolling joints 610, 620 illustrated in FIGS. 2a to 2c as shown particularly in FIGS. 3a and 3b. Combined motion of the two tendon pairs 56, 58 will induce the motion in either the top rolling joint 610 or the bottom rolling joint 620. If a single pair of tendons is moved, a combined motion of both the rolling joints 610, 620 will be induced. Movement of both pairs of tendons together in the same direction will induce the motion in one of the rolling joints only. Similarly, if both of the tendons are moved in the opposite direction the other rolling joint will be moved. By combining the motion of the two tendon pairs it is possible to precisely control the position of each rolling joint 610, 620.

In the joint units illustrated in FIGS. 2a to 2c, and 3a to 3c, another two pairs of tendons 54 will be attached to the joint component 32 in order to control movement of the two rolling joints in the adjacent joint unit.

Figures 2A, 2B, 2C:
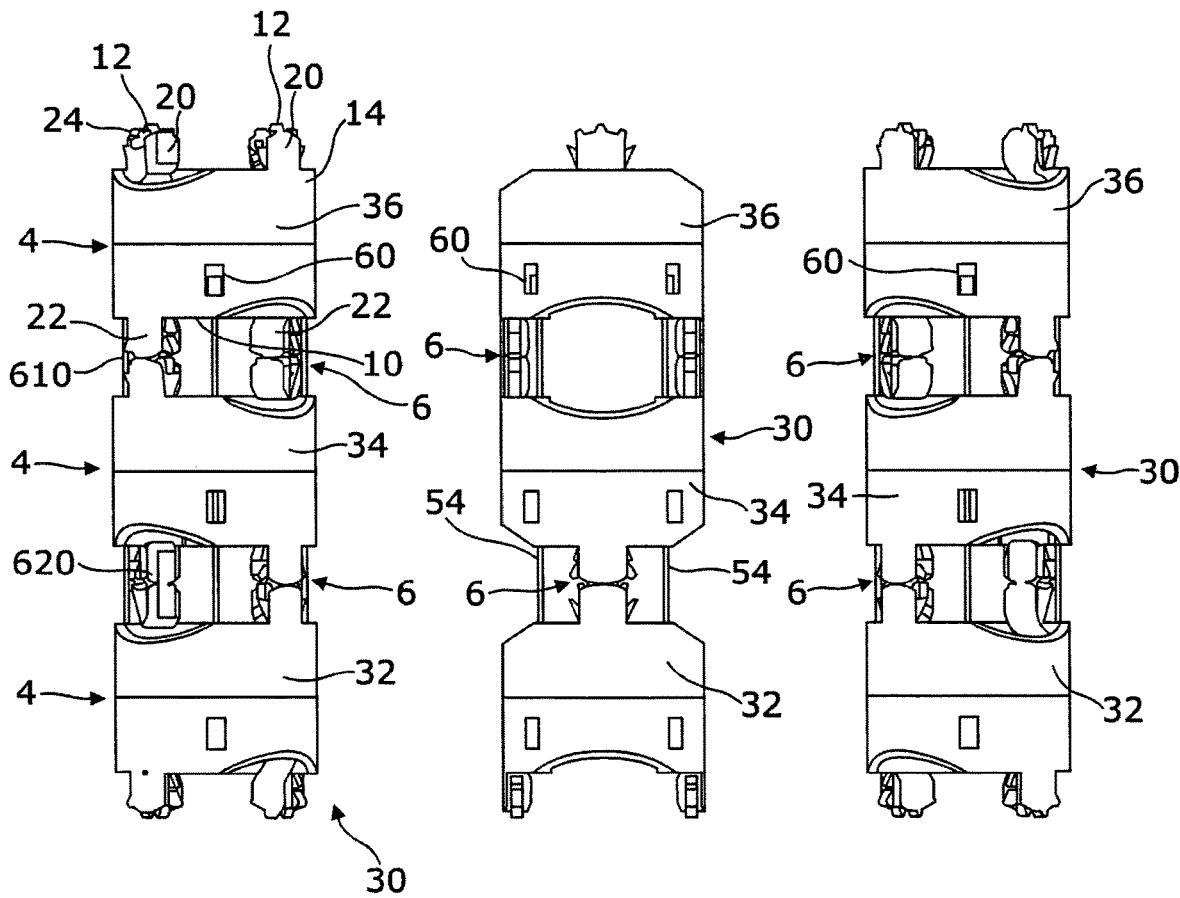
FIGS. 2a to 2c are schematic representations of a joint unit forming part of the surgical instrument in FIGS. 1a and 1b.

In the surgical instrument illustrated in FIG. 1 it will be desired to have twelve pairs of tendons (twenty-four tendons) in total, with two pairs of tendons being attached to every other joint component 4 as described hereinabove with reference to the joint unit 30 shown in FIGS. 2a to 2c.

Each tendon will run through a Bowden cable 70 as shown in FIGS. 5, and 7b for example. This is to allow force transmission to specific points in the body of the surgical instrument 2 and to reduce friction. The Bowden cable 70 will be kept as close as possible to the axis of the surgical instrument 2 in order to limit the stress induced by the rotation of the rolling joint 6. In this embodiment the Bowden cables 70 carrying the tendons 54 will extend through the central portion 48 of the inner channel 46 of each joint component 4, until the tendons reach the joint component 4 to which they are to be attached.

In order to compensate for the variation in path length on each side of a rolling joint 6, the Bowden cables 70 may freely translate individually. This is possible since the base of the Bowden cables is left loose. This feature together with the central location of the Bowden cables 70 may result in a reduction of cross-talk between tendons 54 and will also reduce the risk of herniation.

Once it is necessary to route the tendons 54 to the particular joint component 4 to which they are to be attached, it is advantageous to ensure that the tendons extend as closely as possible to the wall 42 of each joint component to ensure a large force transmission is achieved. The tendons 54 therefore should be routed from a central portion 48 of the inner channel 46 to an outer side of the respective joint components. This is achieved due to the peripheral channels 50 inside the joint component 4 which guide the Bowden cables 70 from the central portion 48 to the wall channel 52 positioned on the wall 42 of the joint component 4.

Figure 12:
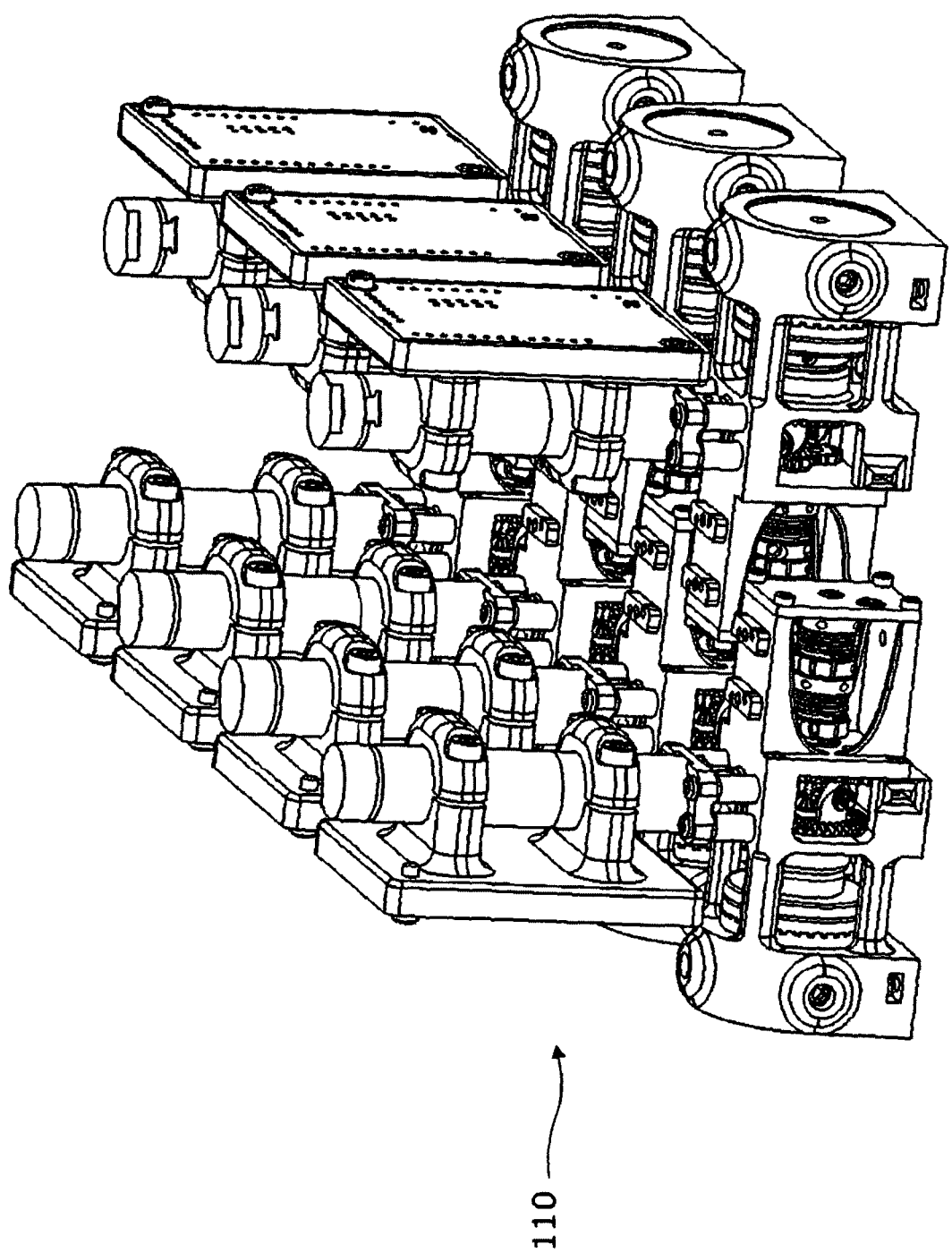
Figure 13:
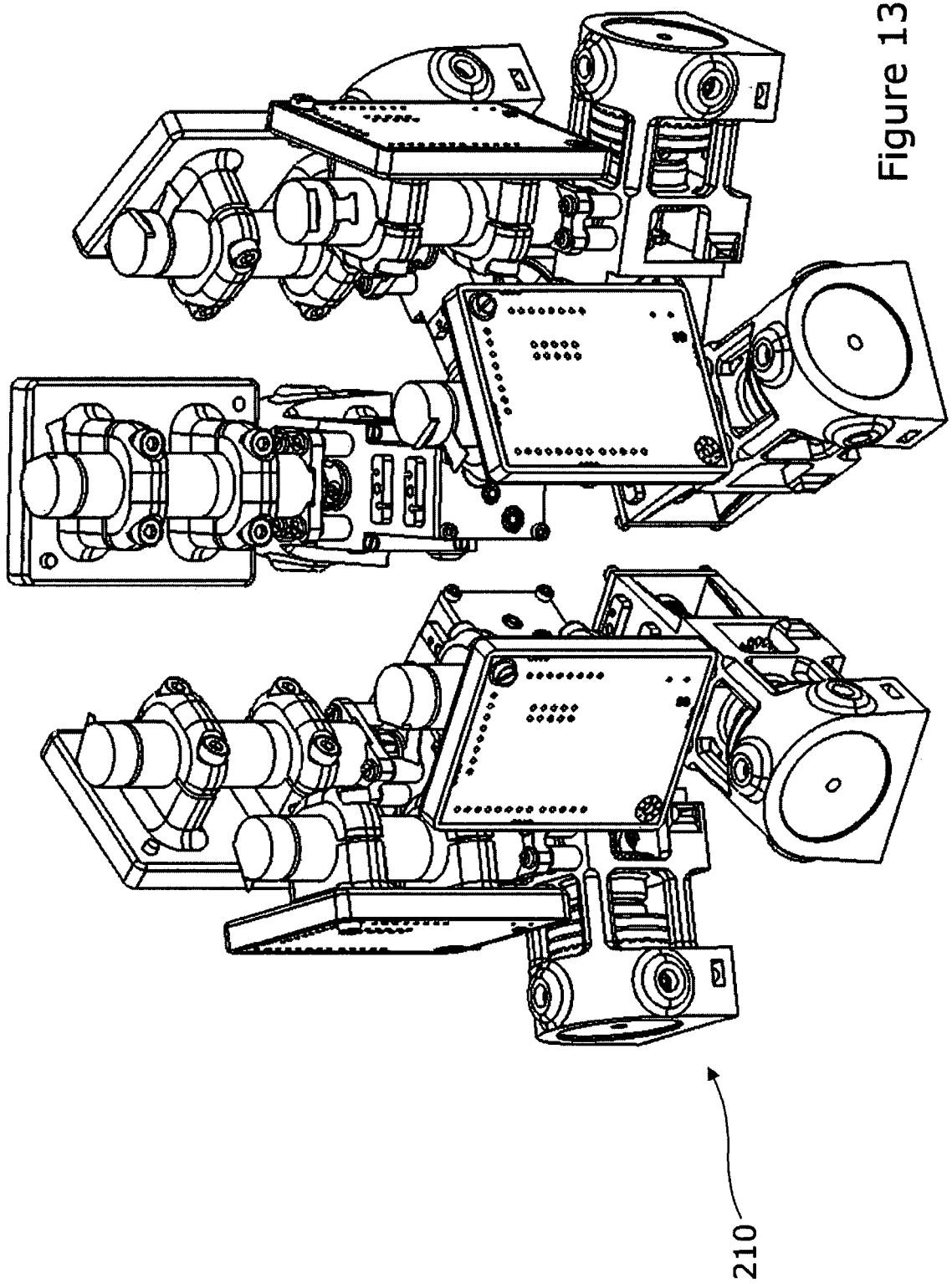

The peripheral channels are also able to retain a tip of the Bowden cable 70 due to a stopper having a smaller hole through which the tendon may pass through. During robotic endoscopy surgery, it may be important to be able to quickly retract the robot in case of unforeseen emergencies. The surgical instrument 2 which is in the form of a snake-like robot is appropriate for use in such surgery. This instrument 2 is equipped in this embodiment with actuator 100 which allows the instrument 2 to switch between three different states. These three states are possible through use of a back drivable actuation pack 110 illustrated in FIG. 12, or back drivable actuation pack 210 illustrated in FIG. 13.

The actuation pack 110 comprises a three-way switch 112 which is shown schematically in FIGS. 8 to 11. In this embodiment of the invention, the three-way switch 112 is a differential mechanism of the type often used in automobiles. The differential mechanism 114 is coupled with an electro-magnetic brake 116 and motor 118 to form the three-way switch. One differential is used for each degree of freedom (DOF) of the instrument 2. In this case therefore seven differentials are required for the seven degrees of freedom show in FIG. 1b. Each actuation pack 110 drives two tendons pairs in an antagonistic actuation. This will generally be achieved using opposite capstans as a tendon is pulled by a first capstan, the corresponding paired tendon is loosened by an opposite capstan. Two tendon pairs are controlled by each actuation pack 110 using four capstans, thus reducing the total number of actuation motors 118 required to control the robot from 13 to 7. The principle of operation of the three modes is described below.

Floppy State

Figure 10:
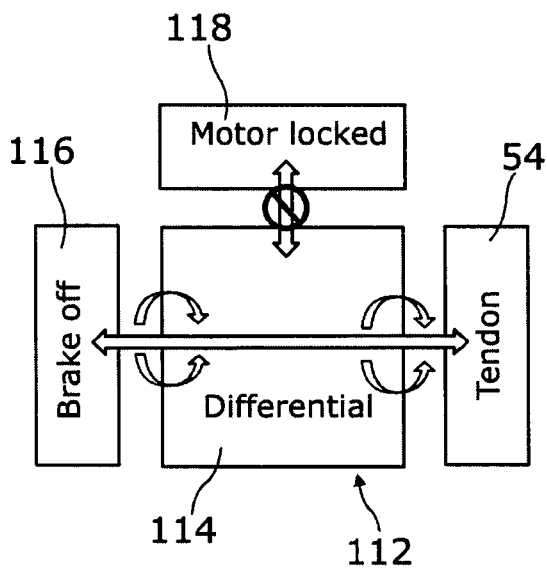

In this mode the body of the surgical instrument 2 is manually back drivable. In this mode all of the tendons 54 of the instrument 2 are disengaged from the motors 118 by releasing the brake 116. This allows the respective joint 6 to rotate freely. This mode is useful for manual insertion or retraction as performed during standard endoscopic procedures. This mode is depicted in FIG. 10.

Actuation State

Figure 11:
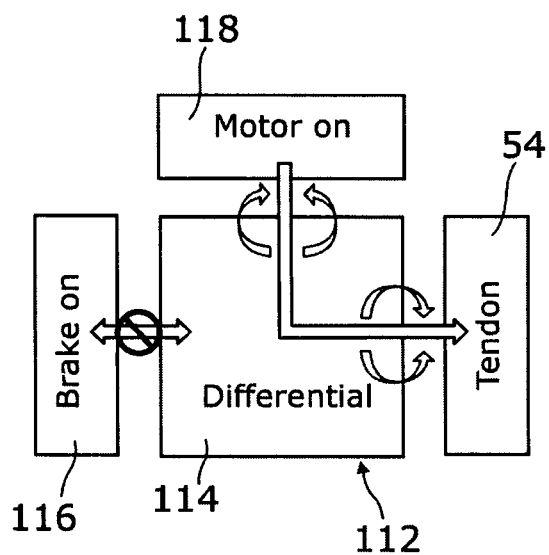

In this mode the body of the instrument 2 is actuated by locking the brake 116 and using the motor 118. This mode can be used for follow-the-leader navigation and inspection of a patient's anatomy. This mode may also be used for motion stabilisation such as breathing motion compensation and target locking whilst working on moving organs. This mode is depicted in FIG. 11.

Stiff State

Figure 9:
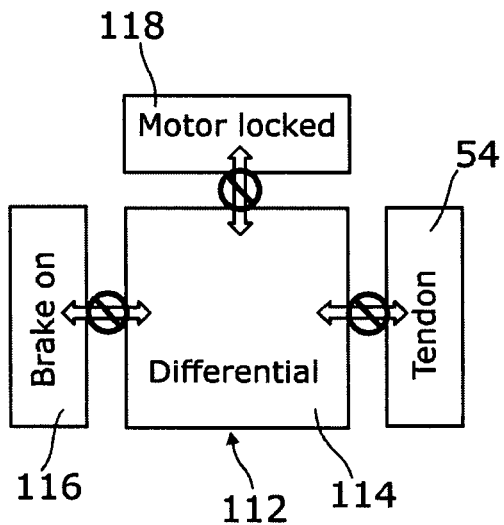

In this mode the body of the instrument 2 is rigid. This offers a stable platform on which to perform tissue manipulation using two surgical instruments 2 passing through available channels within a patient. This state may be accomplished by locking both the brake 116 and the motor 118. This mode is depicted in FIG. 9.

The instrument 2 may be tailor-made to fit individual patients and almost any human anatomy within any particular patient.

Design

In order to provide tailor-made instruments, it is desirable to design the diameter of each joint component 4 and the length of each joint component to provide a suitably dimensioned surgical instrument 2.

The desired parameters are determined from a knowledge of the diameter and bending radius of the passage through which the instrument is to be passed. For example, if the instrument is to be passed through the oesophagus 200 of a patient (FIG. 14), then knowing the dimension of the oesophagus will enable an appropriately dimensioned instrument 2 to be made.

The relevant information may be obtained from pre-operative imaging. The diameter and length of the joint component 4 may then be calculated to ensure safe navigation without collision during operation of the instrument 2. To optimise the rolling joint range of motion an optimisation algorithm is used to optimise the various rolling joint parameters. The optimisation algorithm considers the tendon placement as well as various collisions (tendon-joint collision, joint-joint collision) in the optimisation process. The resulting optimised joint may be made patient specific. An example of such optimisation is set out below.

If the patient's oesophagus is 15 mm in diameter, for example, then the diameter of the joint component 4 should be smaller than 11 mm in order to allow for a 4 mm safety margin.

Figure 14:
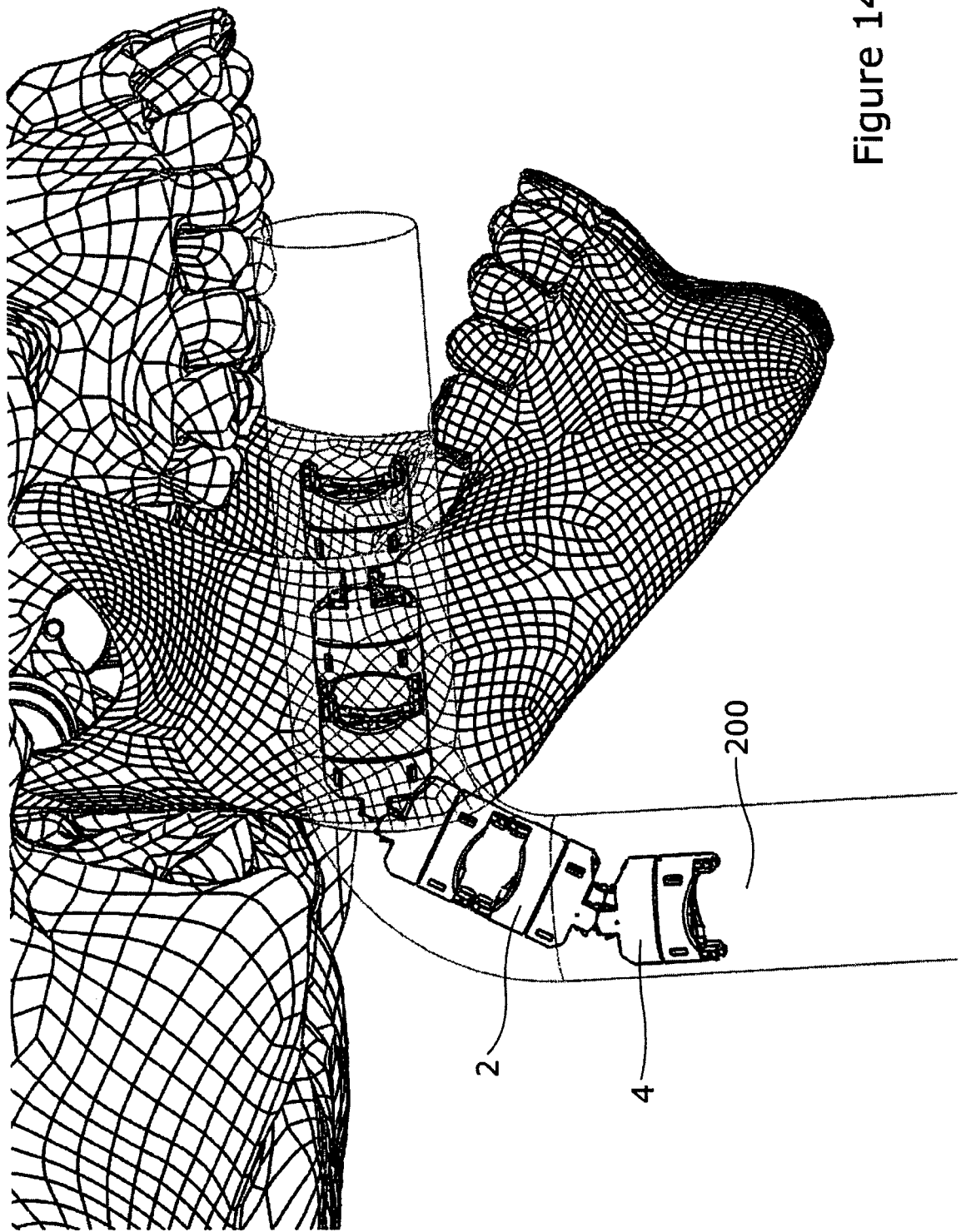
FIG. 14 is a schematic representation showing how the dimensions of the surgical instrument illustrated in FIG. 1a may be calculated in order to fit a particular patient and in this case the oesophagus of a particular patient.

For the joint length, the bending radius of the oesophagus should be known to ensure that two consecutive joints in a straight and aligned configuration will not collide with the anatomy of the patient. This may be achieved in a simulation as shown in FIG. 14 where the maximum length available is calculated at 36.77/2=18.38 mm of joint length.

In the illustrated embodiment, the necessary parameters were determined using a review of human anatomy to match the requirements of a surgical intervention through the oesophagus when considering an average size adult patient.

The identified joint parameters are 16 mm and 18 mm for joint diameter and joint length respectively. This allows two consecutive joints in a straight configuration to pass from the mouth cavity to the oesophagus. Once the input parameters are defined, an algorithm is used to compute the optimised joint parameters such as the rolling joint radius, the rolling joint width, and the tendon position. These parameters are then used to create a template rolling joint design which is automatically updated with the computed parameters and can be rapidly manufactured using 3D printing techniques.

The combination of the rolling joint 6 with the spur gears allows bi-stability and synchronous motion through the surgical instrument 2. The position and the arc of the two rolling joint parts is based on the spur gear parameters, so the rolling joint will match the pitch circle of the spur gears. This is to ensure a correct distance between two mated spur gears and to allow a smooth rolling action. If the rolling joint is too large, this will result in slack when two joint components are engaged with one another. If the rolling joint part is too small, this will result in jerky motion and instability as the teeth of each spur gear will collide with one another.

While the subject matter discussed herein is susceptible to various modifications and alternative constructions, certain illustrated embodiments thereof are shown in the drawings and have been described above in detail. It should be understood, however, that there is no intention to limit the claims to the specific forms disclosed, but on the contrary, the intention is to cover all modifications, alternative constructions, and equivalents falling within the spirit and scope of the claims.

The invention claimed is:

1. A surgical instrument, comprising:
a proximal end;
a distal end; and
a shaft, the shaft comprising a plurality of joint components connected in series, each joint component comprising first and second connectors, which connectors are axially spaced apart from one another at first and second ends of a respective joint component,
wherein the first connector comprises a first rolling surface, and the second connector comprises a second rolling surface, and wherein each joint component comprises a first spur gear extending from the first rolling surface, and a second spur gear extending from the second rolling surface,
wherein a first rolling surface of a first joint component is engageable with a second rolling surface of a second joint component to form a rolling joint, and a second rolling surface of the first joint component is engageable with a first rolling surface of a third joint component, and
wherein each joint component comprises a wall defining a hollow interior and an inner channel extending axially through the joint component, wherein the inner channel of each joint component comprises a central channel portion and a peripheral channel extending from the central channel portion to an inner surface of the outer wall.

2. The surgical instrument of claim 1, wherein each joint component comprises two first connectors and two second connectors, the first connectors being positioned at the first end of the joint component, and the second connectors being positioned at the second end of the joint component, and wherein each joint component comprises two first spur gears and two second spur gears, each spur gear extending from a respective rolling surface.

3. The surgical instrument of claim 2, wherein the two first connectors are positioned opposite to one another at the first end of a respective joint component, and the two second connectors are positioned opposite one another at the second end of the respective joint component, the second connectors being approximately 90 degrees out of phase with the first connectors.

4. The surgical instrument of claim 3, wherein each joint component has a substantially circular cross section, with the two first connectors being diametrically opposed to one another along a first diameter, and the two second connectors being diametrically opposed to one another along a second diameter, the first and second diameters being substantially orthogonal to one another.

5. The surgical instrument of claim 1, wherein each joint component further comprises a wall channel extending axially along an inner surface of the wall.

6. The surgical instrument of claim 5, wherein the peripheral channel of each joint component extends from the central channel to the wall channel of the respective joint component.

7. The surgical instrument of claim 1, comprising a plurality of joint units, each joint unit comprising three joint components forming two rolling joints.

8. The surgical instrument of claim 1, further comprising a drive mechanism for driving the joint components.

9. The surgical instrument of claim 8, wherein the drive mechanism comprises a plurality of tendons.

10. The surgical instrument of claim 8, further comprising an actuator for-operatively connected to the drive mechanism.

11. The surgical instrument of claim 10, further comprising a switch for switchably connecting the actuator to the drive mechanism.

12. The surgical instrument of claim 11, wherein the switch is a three-way switch.

13. The surgical instrument of claim 11, wherein the switch comprises a differential mechanism coupled with an electro-magnetic brake.

14. The surgical instrument of claim 11, wherein the surgical instrument is switchable between a floppy state, an actuation state and a stiff state.

15. A joint component for a surgical instrument, comprising:
first and second connectors axially spaced apart from one another at first and second ends of a respective joint component, wherein the first connector comprises a first rolling surface, and the second connector comprises a second rolling surface, and wherein each joint component comprises a first spur gear extending from the first rolling surface, and a second spur gear extending from the second rolling surface, wherein a first rolling surface of a first joint component is engageable with a second rolling surface of a second joint component to form a rolling joint and a second rolling surface of the first joint component is engageable with a first rolling surface of a third joint component, and wherein each joint component comprises a wall defining a hollow interior and an inner channel extending axially through the joint component, wherein the inner channel of each joint component comprises a central channel portion and a peripheral channel extending from the central channel portion to an inner surface of the outer wall.

16. A joint unit forming part of a surgical instrument, comprising:

three joint components forming two rolling joints, each joint component, comprising:

first and second connectors axially spaced apart from one another at first and second ends of a respective joint component, wherein the first connector comprises a first rolling surface, and the second connector comprises a second rolling surface, and wherein each joint component comprises a first spur gear extending from the first rolling surface, and a second spur gear extending from the second rolling surface, wherein a first rolling surface of a first joint component is engageable with a second rolling surface of a second joint component to form a rolling joint and a second rolling surface of the first joint component is engageable with a first rolling surface of a third joint component, and wherein each joint component comprises a wall defining a hollow interior and an inner channel extending axially through the joint component, wherein the inner channel of each joint component comprises a central channel portion and a peripheral channel extending from the central channel portion to an inner surface of the outer wall.

17. A method for operating a surgical instrument, comprising the steps of:

inserting the surgical instrument into a patient via a natural orifice or incision, the surgical instrument including:
a proximal end;
a distal end; and
a shaft, the shaft comprising a plurality of joint components connected in series, each joint component comprising first and second connectors, which connectors are axially spaced apart from one another at first and second ends of a respective joint component, wherein the first connector comprises a first rolling surface, and the second connector comprises a second rolling surface, and wherein each joint component comprises a first spur gear extending from the first rolling surface, and a second spur gear extending from the second rolling surface, wherein a first rolling surface of a first joint component is engageable with a second rolling surface of a second joint component to form a rolling joint and a second rolling surface of the first joint component is engageable with a first rolling surface of a third joint component, and wherein each joint component comprises a wall defining a hollow interior and an inner channel extending axially through the joint component, wherein the inner channel of each joint component comprises a central channel portion and a peripheral channel extending from the central channel portion to an inner surface of the outer wall;

switching the instrument to an actuation state;
carrying out a required medical procedure; and then
removing the instrument from the patient.

18. The method of claim 17, further comprising an initial step, carried out before the step inserting the surgical instrument, for switching the instrument to the floppy state.

19. The method of claim 17, further comprising an initial step, carried out before the step of inserting the surgical instrument, for switching the instrument to the stiff state.

20. The method of claim 17, further comprising a step carried out after the step of carrying out a required medical procedure of switching the instrument to a floppy state to thereby remove the instrument from the patient.

21. The method of claim 17, further comprising a step carried out after the step of carrying out a required medical procedure of switching the instrument to a stiff state to thereby remove the instrument from the patient.

* * * * *